(12) United States Patent
Mathews et al.

(10) Patent No.: US 11,186,852 B1
(45) Date of Patent: Nov. 30, 2021

(54) LOW PH PROCESS FOR FERMENTATION OF SUGARS FROM CARBOHYDRATES FOR THE PRODUCTION OF ORGANIC ACIDS AND BIODEGRADABLE DEICERS

(71) Applicants: Alexander P. Mathews, Manhattan, KS (US); Sathyanarayanan Sevilimedu Veeravalli, Sydney (CA)

(72) Inventors: Alexander P. Mathews, Manhattan, KS (US); Sathyanarayanan Sevilimedu Veeravalli, Sydney (CA)

(73) Assignee: Alexander P. Mathews, Manhattan, KS (US)

( * ) Notice: Subject to any disclaimer, the term of this patent is extended or adjusted under 35 U.S.C. 154(b) by 0 days.

(21) Appl. No.: 16/227,909

(22) Filed: Dec. 20, 2018

Related U.S. Application Data (60) Provisional application No. 62/611,365, filed on Dec. 28, 2017.

(51) Int. Cl.
| | | |
|---|---|---|
| *C12P 7/56* | (2006.01) |
| *C09K 3/18* | (2006.01) |
| *C12P 7/52* | (2006.01) |
| *C12P 7/18* | (2006.01) |
| *C12P 7/54* | (2006.01) |
| *C12P 39/00* | (2006.01) |

(52) U.S. Cl.
CPC .................. *C12P 7/56* (2013.01); *C09K 3/18* (2013.01); *C12P 7/18* (2013.01); *C12P 7/52* (2013.01); *C12P 7/54* (2013.01); *C12P 39/00* (2013.01)

(58) Field of Classification Search
None
See application file for complete search history.

(56) References Cited

U.S. PATENT DOCUMENTS

| | | | |
|---|---|---|---|
| 6,475,759 B1 | 11/2002 | Carlson et al. | |
| 2005/0281917 A1* | 12/2005 | Charley | A23K 30/18 426/53 |
| 2014/0308718 A1* | 10/2014 | Sauer | C12P 7/56 435/126 |

* cited by examiner

*Primary Examiner* — Blaine Lankford (57) ABSTRACT

This disclosure provides methods for fermentation of sugar substrates by acid-tolerant bacteria for producing acetic and lactic acids, and methods for further processing of these products to obtain acetate and propionate biodegradable deicers. Methods are also disclosed on the use of acid tolerant bacteria to produce acetate and propylene glycol deicing compounds.

17 Claims, 7 Drawing Sheets

Fig. 1. General schematic for bioconversion of sugars to acetic and lactic acid

Fig. 2a. Bioconversion of xylose to acetic and propionic acids

Fig. 2b. Bioconversion of glucose to acetic and propionic acids

Fig. 3. Bioconversion of lignocellulosic sugars to acetic and propionic acids

Fig. 4. Bioconversion of lactose and whey containing lactose to acetic and propionic acids Fig. 5. Fermentation of xylose to lactate and acetate by *L. buchneri* at pH 4.2

Fig. 6. Fermentation of glucose to lactate and acetate by *L. buchneri* at pH < 4

Fig. 7. Fermentation of glucose and xylose to lactate and acetate by *L. buchneri* at pH < 4

Fig. 8. Fermentation of lactose to lactate, acetate, propylene glycol, and ethanol by *L. buchneri* at pH < 4

Fig. 9. Fermentation of propylene glycol (PG) to propionate and acetate by *L. diolivorans* to pH ~ 4

Fig. 10. Fermentation of lactate to propionate and acetate by *P. acidipropionici* at pH ~ 5.5

Fig. 11. Fermentation of xylose to propionate and acetate by *P. acidipropionici* at pH ~ 5

Fig. 12. Continuous immobilized cell fermentation of xylose to lactic and acetic acids by *L. buchneri* at pH 4.2 and initial substrate of 40 g L$^{-1}$ Fig. 13. Fed-batch fermentation of xylose using *L. buchneri* immobilized in cheese cloth at pH 4.2

Fig. 14. Fermentation of whey powder using *L. buchneri* at pH<4.0

LOW PH PROCESS FOR FERMENTATION OF SUGARS FROM CARBOHYDRATES FOR THE PRODUCTION OF ORGANIC ACIDS AND BIODEGRADABLE DEICERS

This invention was made with government support under Award No. 1600075, CBET Division, National Science Foundation.

BACKGROUND OF THE INVENTION

1. Field of the Invention

The present invention is broadly concerned with a low pH fermentation process for the production of acetic acid and lactic acid, and acetate and propionate road deicers that are substantially less expensive than current methods for the production of acetic and lactic acids, and the production of biodegradable deicers such as calcium acetate (CA), magnesium acetate (MA), calcium magnesium acetate (CMA), and potassium acetate (KA). The process can be used to produce acetic acid and biodegradable deicers containing acetate alone, or biodegradable deicers containing a mixture of acetate and propionate salts. This invention particularly concerns with a fermentation process utilizing acid-tolerant bacteria that can produce acetic and lactic acids at low pH values where extraction of the acids is efficient, and subsequent fermentation of the lactic acid to propionic and acetic acids. The process utilizes heterofermentative *Lactobacillus buchneri* strains in the first stage, and after separation of the acetic and lactic acids, the lactic acid is further fermented to propionic and acetic acids using propionibacteria. Depending on the substrate sugars utilized, this low pH process can also produce acetic acid and lactic acid, and acetate, propionate, and propylene glycol as deicers.

2. Description of the Prior Art

Acetic acid is an important raw material in the chemical industry with uses in the production of plastics, latex paints, adhesives, and acetic anhydride with end uses in the pharmaceutical industry, and in the production of acetate esters and other miscellaneous chemicals. It is also used in the production of deicers such as calcium acetate (CA), magnesium acetate (MA), calcium magnesium acetate (CMA), and potassium acetate (KA) for deicing roads and airport runways under wintry weather conditions. Acetic acid is synthetically produced by the carbonylation of methanol as disclosed in several patents, for example, in U.S. Pat. No. 9,695,101. CMA is currently produced by reacting synthetic acetic acid with dolomite or other calcium and magnesium salts, and KA is produced by reacting synthetic acetic acid with potassium salts. The costs of acetic acid and deicers produced using the synthetic process are quite high due to the high pressure and temperature required in the carbonylation process used to produce acetic acid.

Acetic acid is also produced using a two-step fermentation process wherein yeast fermentation of sugars is used to produce alcohol, and the alcohol is oxidized aerobically by *Acetobacter* species to obtain 5% to 8% acetic acid. This process is not economical for large scale acetic acid or acetate deicer production. Anaerobic fermentation can be used to convert a variety of sugars into acetic acid. However, the product acid concentrations are low since the acid is inhibitory to cell growth. Moreover, the optimum pH of operation is around 7, and at this pH the extraction efficiency of the acid from the fermentation broth is low. The bioreactor needs to be heated to 55° C. to 60° C., and strict anaerobic conditions must be maintained. The anaerobic bacteria that have been studied for acetic acid and acetate deicer production include *C. thermoaceticum* (Marynowski et al, 1983; Shah et al, 1997), and *M. thermoautotrophica* (Talabadron et al, 2000). These studies have shown that acid productivities and product acid concentrations are low with these acetogens, requiring higher capital costs for the reactor and higher operating costs to maintain the reactor at 55° C. to 60° C. Moreover, the acid recovery costs are high due to the low acid concentration and the low extraction efficiencies at pH 6 to 7.

SUMMARY OF THE INVENTION

The present invention provides a novel method for the production of acetic acid, acetate deicing salt, and mixed acetate and propionate deicing salts. It also provides a method for producing acetic acid, lactic acid, and propylene glycol as platform chemicals depending on the substrate sugar or biomass hydrolysate used in the fermentation. This invention is concerned with fermentations using acid-tolerant bacteria to produce high concentrations of acetic and propionic acids at low pH values. This is particularly beneficial in downstream processing for the separation of the organic acids from the fermentation broth. Acid extraction efficiencies are much higher at the low pH values used in the disclosed fermentation process.

The process provided herein includes the cultivation of acid-tolerant bacteria predominantly from the *Lactobacillus* group that can produce acetic acid, and lactic acid predominantly in the acid form. Acid-tolerant implies that the bacteria are not inhibited by the acid end products that allow fermentation to proceed at pH values less than 4.3. The acid tolerant bacteria are capable of producing at least 30 g/L of free lactic acid and 25 g/L of free acetic acid with a nutrient medium containing xylose as the substrate. The acid-tolerant bacteria are also capable of using glucose or lactose as substrates. In the former case, the products of fermentation include lactate, acetate, and ethanol, and in the latter case the products include lactate, propylene glycol, acetate, and relatively small amounts of ethanol. The aforementioned sugars are not all inclusive of the sugars and biomass hydrolysates that can be used in the low pH fermentation process.

The process provided herein includes the extraction and separation of the lactic and acetic acids from the broth using available separation methods including the use of amine extractants or using ion-exchange resins that preferentially exchange one or the other acids. The acetic acid separated can be concentrated to obtain acetic acid product or it can be further reacted with calcium and/or magnesium salts to produce calcium and magnesium acetate dicing salts. Also, potassium salt can be used to produce potassium acetate deicer.

The process provided herein also includes the subsequent fermentation of the lactic acid to propionic and acetic acids using Propionibacteria. The mixed acids are further reacted with calcium and/or magnesium salts to produce mixed deicing salts containing calcium and magnesium propionate (CMP, CP, or MP), and calcium and magnesium acetate (CMA, CA, or MA) deicers. Similarly, KP or KA deicers can be produced. As taught in U.S. Pat. No. 5,324,442, CMP is equally effective as a biodegradable deicing compound compared to CMA.

The process provided herein, is capable of using a variety of sugar substrates, wastes containing sugars, or biomass and biomass waste hydrolysates in the nutrient medium. The sugar substrates can be glucose, xylose, lactose or other sugars and biomass hydrolysates. The end products in these cases are predominantly lactate and acetate, but may also include ethanol and propylene glycol. Process schematics are provided specifically for the conversion of xylose, glucose, lactose, and whey permeate, to lactate and acetate, or lactate, acetate, ethanol, and traces quantities of propylene glycol, or propylene glycol, acetate, lactate and trace quantities of ethanol, respectively depending on the feed substrate used. Process schematics are provided herein for the conversion of ethanol to acetic acid or acetate deicer, and for the separation of propylene glycol from the broth for use as aircraft deicer, or for the further conversion of propylene glycol to propionate deicer.

DETAILED DESCRIPTION OF THE PREFERRED EMBODIMENT

The present process allows the efficient production of lactic and acetic acids at high concentrations via incubation of acid-tolerant heterofermentative bacteria in a suitable nutrient medium. The bacterial species utilized, *Lactobacillus buchneri*, can be isolated from a variety of sources including silages, tomato pomace, cucumber pickling, ethanol production, etcetera. *L. buchneri* is chosen as the preferred organism due to its ability degrade a variety of sugar substrates including waste byproducts and lignocellulosic hydrolysates to acetic and lactic acids, and propylene glycol as major products depending on the sugar utilized.

Figure 1:
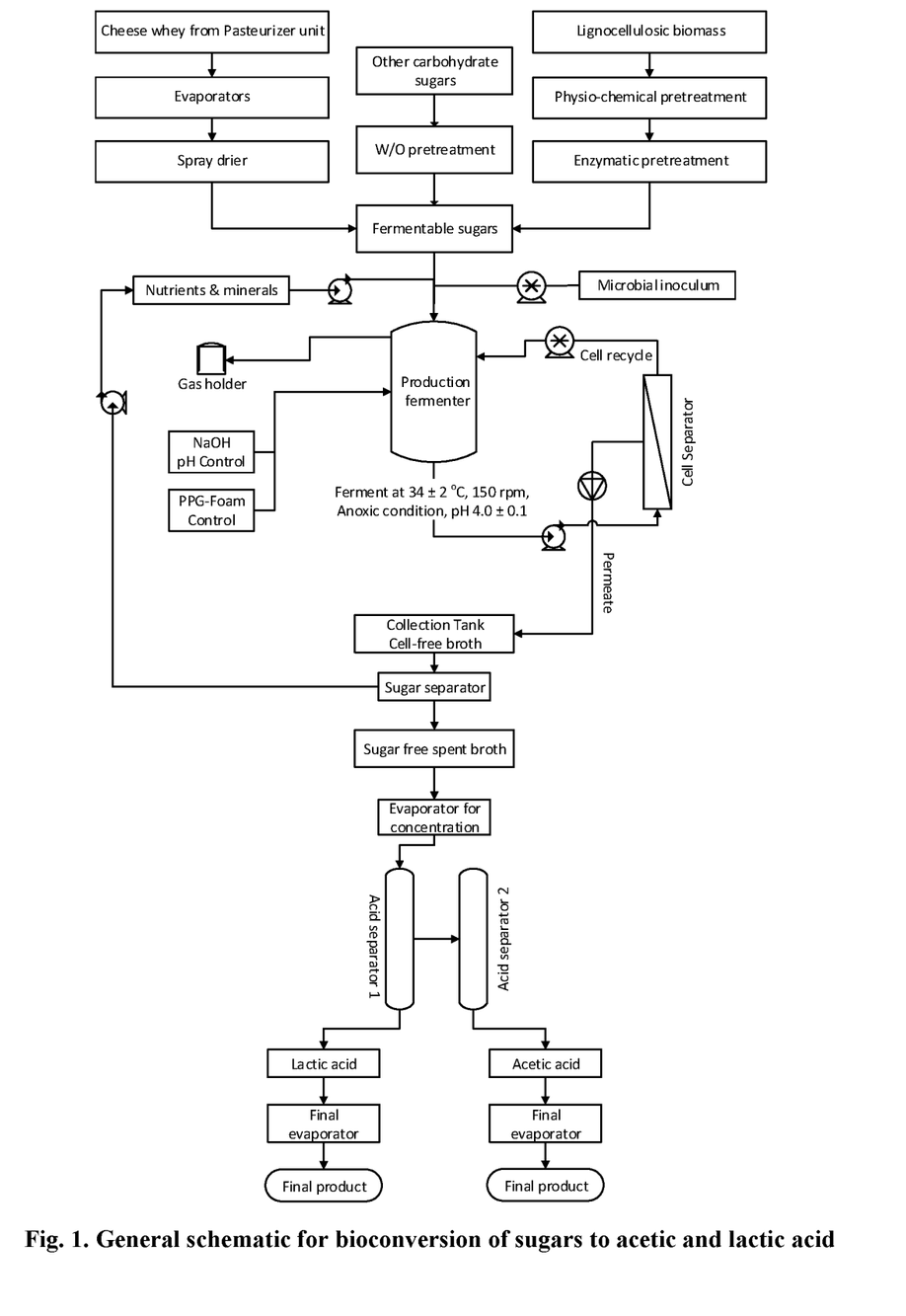
FIG. 1 is a process flowsheet that displays the various operations on the raw biomass materials that will be conducted at low pH to produce acetic and lactic acids as products, and the separation processes to obtain separate streams of acetic acid and lactic acid as products. A variety of biomass wastes including whey permeate containing lactose, hydrolysates of lignocellulosic materials containing sugars such as glucose, xylose, or other sugars can be used as substrates for the production of the organic acids.

FIG. 1 provides a general schematic wherein a number of alternatives are provided for the feed substrate. One of the alternatives is the use of whey lactose from cheese processing or yoghurt production operations which can be preconcentrated and fermented in the bioreactor at a pH ~4 and a temperature of ~34° C. Sugars such as glucose and xylose can be fed to the fermenter without pretreatment. Lignocelluosic biomass and wastes will undergo pretreatment including acid or enzymatic hydrolysis prior to being fed to the bioreactor. A cell separator is used to separate the cells from the fermentation broth, and the cells are recycled to the fermenter to maintain a high cell concentration in the reactor. The unused sugar in the fermentation broth is separated from the product and recycled. The lactic and acetic acids are separated in extractors, and the products can be concentrated to obtain lactic acid and acetic acid as products.

The cell separator in FIG. 1 can be chosen from a variety of solid-liquid separation devices including a settler, centrifuge, ceramic or polymeric membrane filter, and a variety of mechanical filters including, but not limited to, belt filter, vacuum filter, and filter press.

Figure 2A:
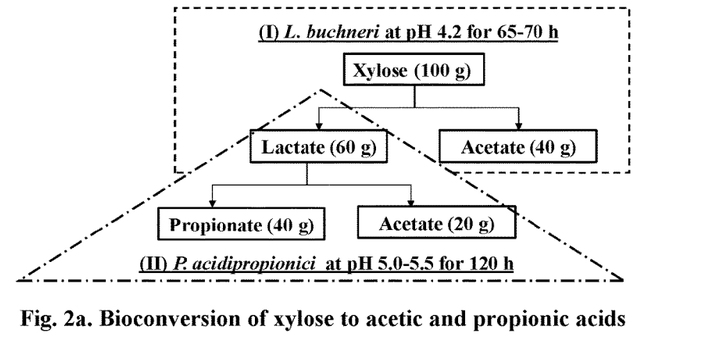
FIG. 2a is a process schematic for the conversion of xylose to lactate and acetate as products. Lactic and acetic acids can be separated as indicated in FIG. 1, or lactate can be further converted to acetate and propionate as end products. Acetate and propionate are desirable as end products to produce biodegradable deicer products CMA, CMP, KA, and KP.
Figure 5:
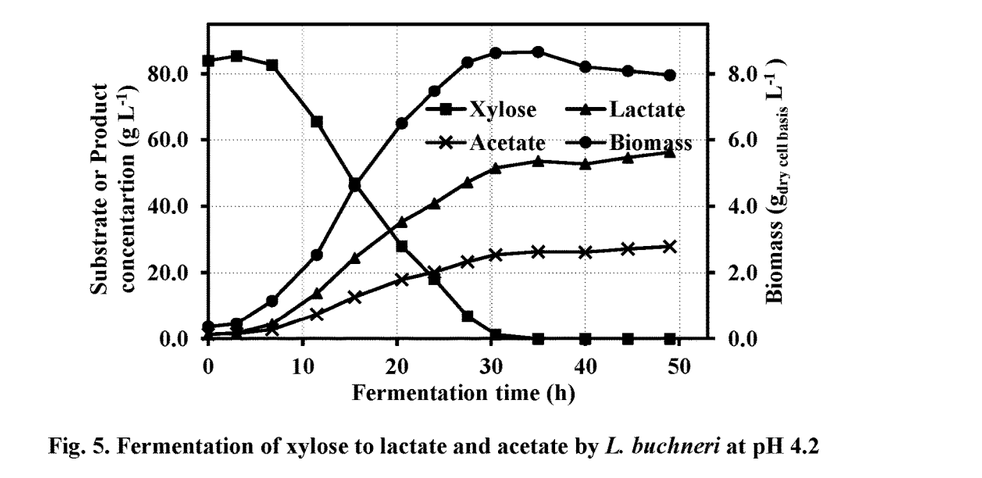
FIG. 5. This graph shows fermentation process data for the conversion of xylose to lactate and acetate at pH 4.2.
Figure 7:
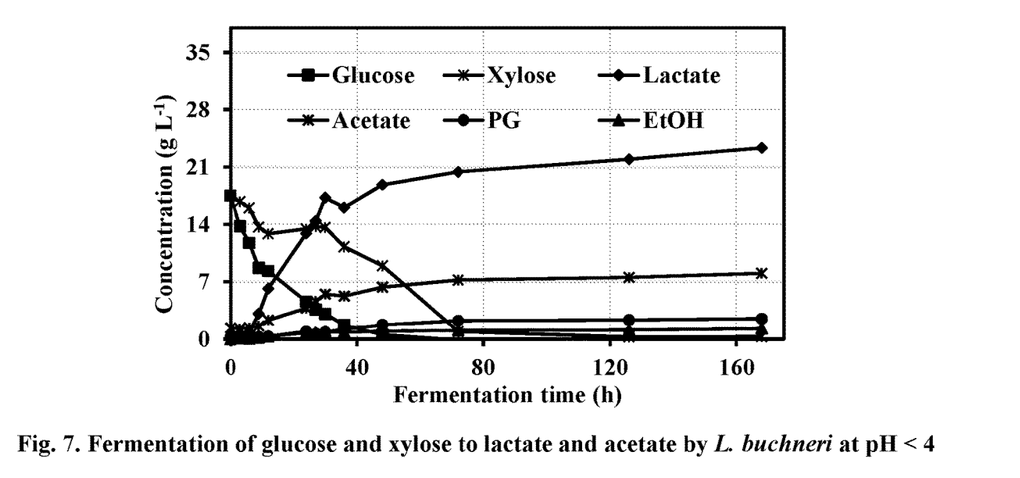
FIG. 7. This graph shows the conversion of a combination of glucose and xylose as substrate to give lactate, acetate as major products, and propylene glycol and ethanol as minor products. The final pH of this fermentation was less than 4.
Figure 10:
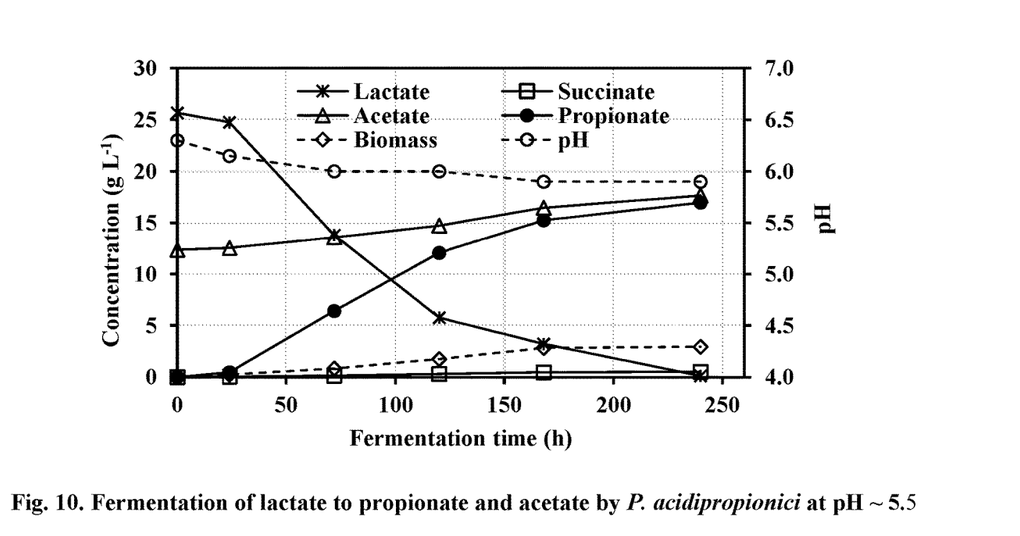
FIG. 10. This graph shows conversion of lactate from FIG. 1, 2, 3 or 4 to propionate and acetate at pH ~5.5.
Figure 11:
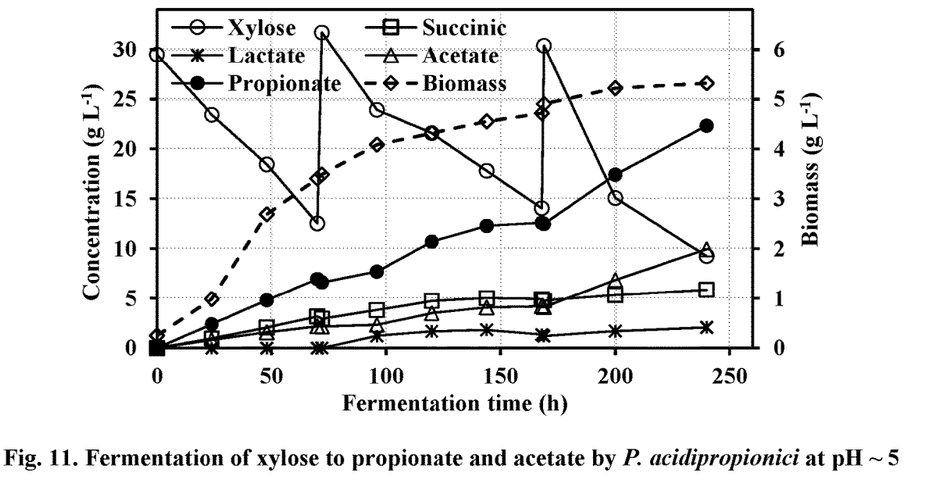
FIG. 11. This graph shows the conversion of xylose to propionate at pH close to 5.

FIG. 2a is a schematic for the fermentation of xylose to lactate and acetate at pH ~4.2 to lactic and acetic acids, separation of lactate and acetate, and the further conversion of lactate to propionate and acetate by *Propionibacterium acidipropionici* at pH ~5.5. In this two-stage process, approximately 60 g of acetate and 40 g of propionate can be obtained from 100 g of xylose for use in the production of acetate and propionate deicing salts. The acetate and lactate produced in the first stage can also be separated and sold as products without further conversion by *P. acidipropionici*. FIG. 5 shows typical results obtained from the fermentation of xylose by *L. buchneri* at pH<4. The fermentation of glucose or xylose to lactate (FIG. 7) and further conversion of product lactate to propionate and acetate by *P. acidipropionici* is shown in FIG. 10, and also is the subject of U.S. Pat. No. 5,324,442.

Figure 2B:
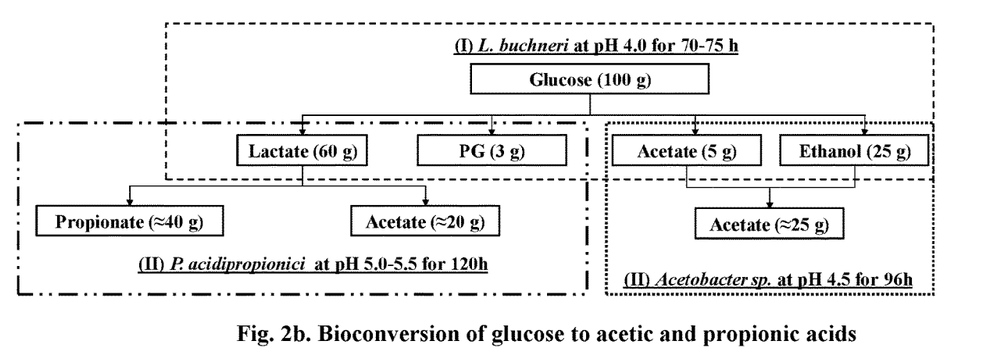
FIG. 2b is a process schematic for the conversion of glucose as substrate to lactate, acetate, ethanol, and propylene glycol, and further conversion of these products to acetic and propionic acids.
Figure 6:
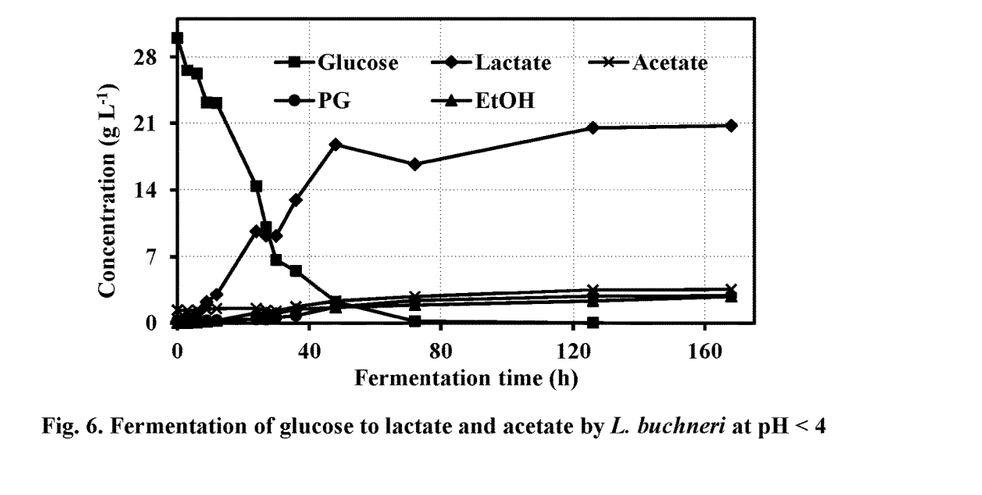
FIG. 6. This graph shows the conversion of glucose as substrate to lactate and acetate and small amounts of propylene glycol and ethanol with a final fermentation pH of 3.75.

FIG. 2b is a schematic for the conversion of glucose to acetate and propionate by a group of bacterial species. The products of bioconversion in the first stage using *L. buchneri* at pH ~4 include lactate, acetate, ethanol and propylene glycol. After separation of the lactate from the broth, the ethanol is converted using *Acetobacter* to acetate at pH ~4.5. The lactate can also be further fermented using *P. acidipropionici* to obtain propionate and acetate. In this case, 100 g of glucose will yield approximately 50 g of acetate and 40 g of propionate. FIG. 6 shows typical results of glucose the conversion lactate, ethanol and acetate with small amounts of propylene glycol and a final fermentation pH of 3.6.

Figure 3:
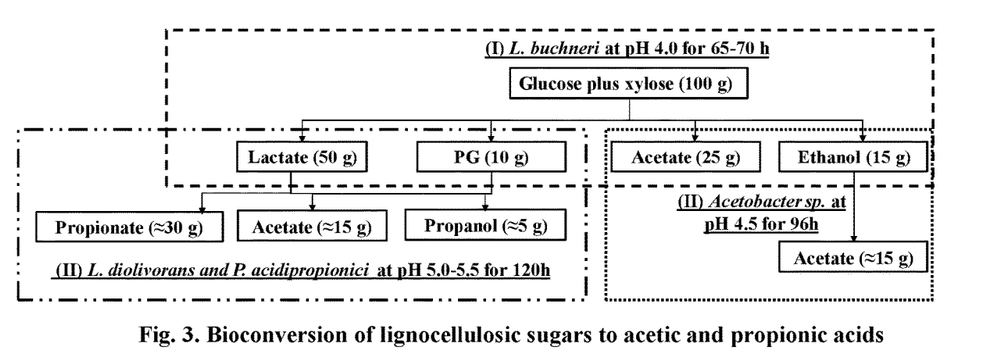
FIG. 3 is a process flowsheet for the conversion of glucose and xylose to lactate, acetate, ethanol, and propylene glycol (PG) as products, and further fermentation of the PG and ethanol products to propionic and acetic acids. These acid products are desirable to produce CMA, CMP, KA, and KP deicing compounds. The hydrolysis of woody biomass produces glucose and xylose as the predominant sugars in the hydrolysate, and this flowsheet illustrates the combined utilization of theses sugars as substrate.
Figure 9:
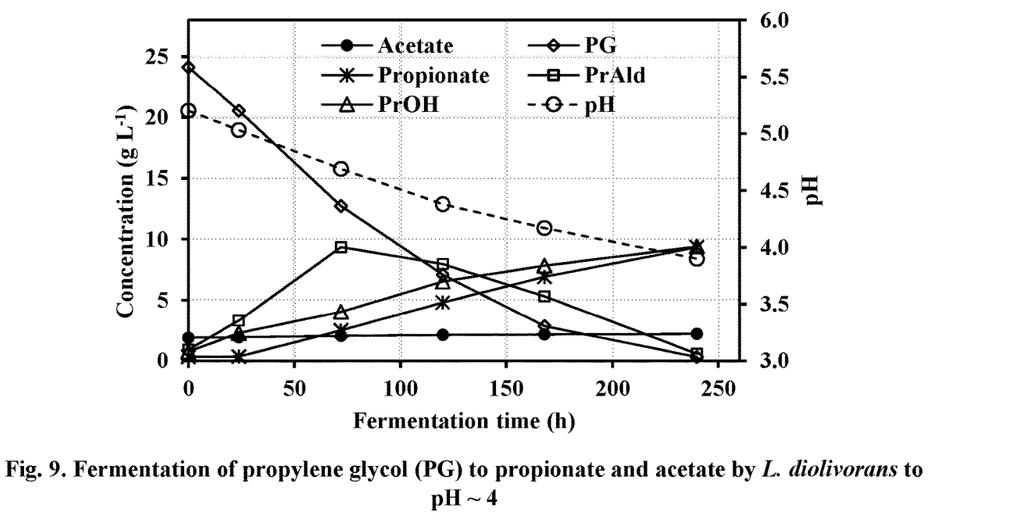
FIG. 9. This graph shows the low pH conversion of propylene glycol from fermentation in FIG. 2 to propionate as product.

FIG. 3 shows a general schematic for glucose and xylose, the predominant sugars from the hydrolysis of lignocellulosic materials, as the feedstock. In the bioconversion of mixed sugars by *L. buchneri* at pH ~4, lactic acid (50%) and acetic acid (25%) are the primary products, but there is also 10% of propylene glycol, and 15% of ethanol in the product. The propylene glycol is further converted to propionate and propanol at pH ~4 by *Lactobacillus diolivorans* (see FIG. 9). The ethanol is further converted to acetate by *Acetobacter* at pH ~4.5. The lactate is converted to acetate and propionate by *P. acidipropionici* at pH ~5.5. This process will produce 55 g of acetate and 30 g of propionate from 100 g of mixed sugar feed.

Figure 4:
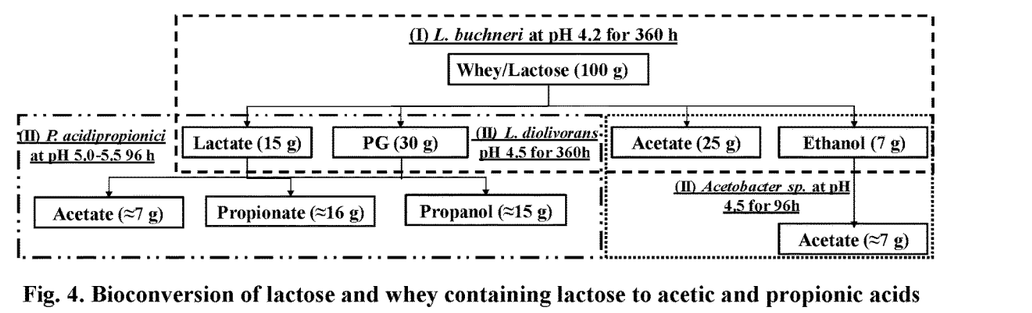
FIG. 4 is a process flowsheet for the conversion of the lactose or whey containing lactose to lactate, acetate, ethanol, and propylene glycol (PG) as products, and further fermentation of the lactate, PG and ethanol products to propionic and acetic acids. These acid products are desirable to produce CMA, CMP, KA, and KP deicing compounds.
Figure 8:
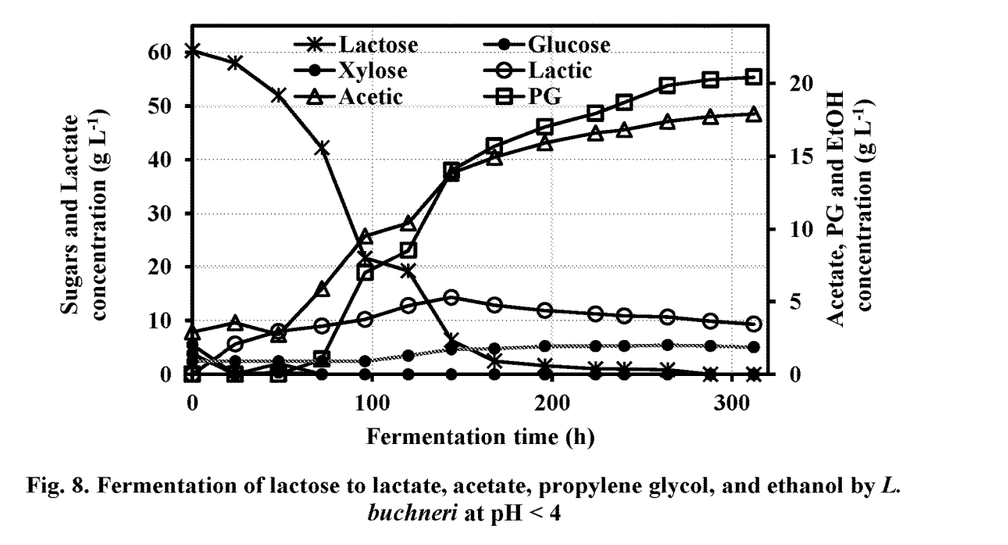
FIG. 8. This graph shows conversion of lactose to lactate, acetate, and propylene glycol as major products and ethanol as a minor product. The final pH of this fermentation was less than 4.
Figure 14:
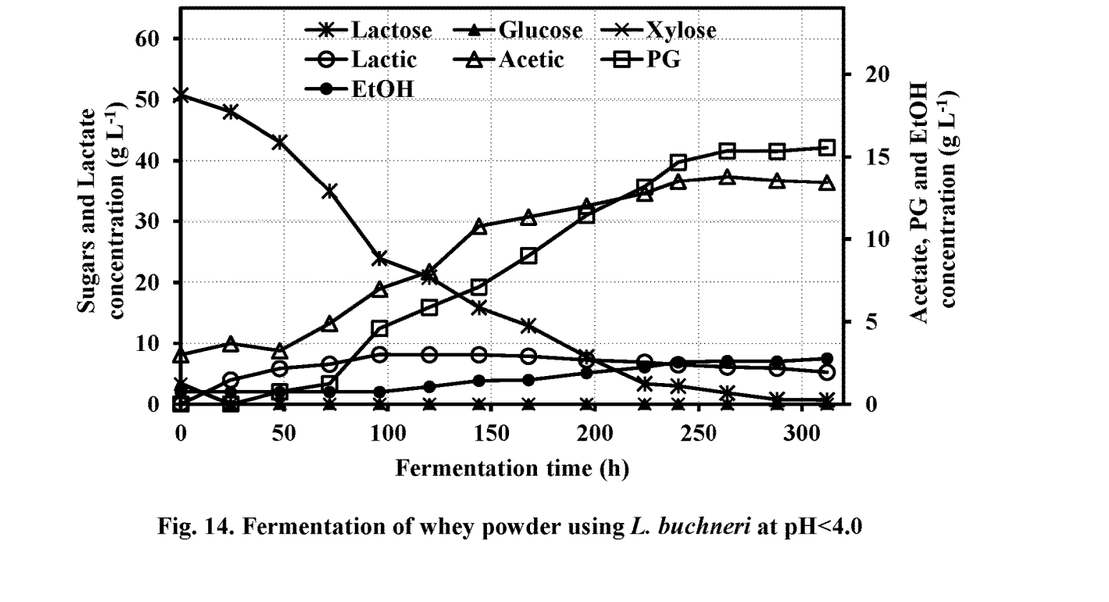
FIG. 14. This graphs shows the conversion of whey permeate powder by L. buchneri to propylene glycol and acetic acid as major products, and lactic acid and ethanol as minor products at pH<4.0.

FIG. 4 shows schematic conversion of lactose and whey containing lactose to lactate, acetate and propylene glycol as major products. After separation of acetate, the lactate can be further converted to propionate and acetate by *P. acidipropionici* at pH ~5.5, while propylene glycol is further oxidized to propionate and propanol at pH ~4 by *Lactobacillus diolivorans* (see FIG. 9). This process would yield about 39 g of acetate and 16 g of propionate from 100 g of lactose. A typical fermentation of lactose and whey is shown in FIGS. 8 and 14.

The steps identified in FIGS. 2 to 4 are to maximize the yield of propionate and acetate that can be reacted with calcium, magnesium, or potassium salts to produce acetate and propionate deicing chemicals. However, if the goal is to produce lactic and acetic acids, the subsequent fermentation steps using *P. acidipropionici, Acetobacter,* or *L. diolivorans* may be omitted.

The pH of the broth during fermentation can be expressed in several different ways, e.g., in terms of the average fermentation pH or the final pH. The present process is capable of producing high levels of the primary products, lactic acid and acetic acid, at an average pH no greater than 4.3. The final pH in the uncontrolled pH fermentation is a function of the initial pH and the sugar concentration in the broth. A final pH as low as 3.1 was tolerated by *L. buchneri* with a starting pH of 4.5 and initial mixed glucose and xylose concentration of 20 g/L. The present process allows the production of lactic and acetic acids at a pH no more than 4.3, and preferably no more than 4.0 for the complete conversion sugar substrates. The further conversion of lactate to propionate and acetate by *P. acidipropionici,* is accomplished at a pH no greater than 5.5. The conversion of propylene glycol to propionate, if desired, can be accomplished using *L. diolivorans* at pH no greater than 4.0. The conversion of ethanol in the products, if desired, can be conducted at a pH no greater than 4.5.

The fermentation temperature for the acid-tolerant bacterium *L. buchneri* can range from 30° C. to 40° C. A temperature of incubation of 37° C. is preferred as the optimal temperature.

The present fermentation process can be conducted in batch mode, fed-batch by mode by providing feed at periodic intervals, or in a continuous mode with continuous feed and withdrawal of product. In all types of fermentation operations the bacteria can be freely suspended in liquid or in immobilized form where the bacteria are attached to carriers. Immobilization can be accomplished in a variety of ways with carriers including, but not limited to, porous or nonporous surfaces including fibers and beads, calcium alginate beads, or fibrous cloth material.

*L. buchneri* can utilize a number of carbon and energy sources for the growth and the generation of products. These include, but are not limited to, glucose, xylose, and lactose, or a combination of sugars, or sugars from the hydrolysis of starch and lignocellulosic materials. The nutrient medium required typically contains effective amounts of sources of carbon, nitrogen, phosphorus, minerals, and trace elements. Trace elements are elements needed in minute quantities for cell growth and product formation. Composition of the nutrient medium used is shown in Table 1. The nitrogen source in the medium can be replaced with other inexpensive nitrogen sources such as corn steep liquor and soy peptone. Previous studies using corn steep liquor with *Lactobacillus* sp., has been reported (Vadlani et al, 2008). In addition, with whey as substrate, the 6% to 13% protein present in whey can be used as a source of nitrogen.

TABLE 1

| Incubation nutrient medium | |
|---|---|
| Compound | Concentration (g $L^{-1}$) |
| Yeast extract | 5.0 |
| Peptone | 3.0 |
| Casamino acids | 2.0 |
| Lab-Lemco Powder (oxoid) | 2.0 |
| Dipotassium hydrogen phosphate | 1.0 |
| Ammonium dihydrogen phosphate | 2.0 |
| Sodium acetate trihydrate | 1.0 |
| Magnesium sulfate heptahydrate | 0.2 |
| Manganese(II) Sulfate Tetrahydrate | 0.05 |
| Copper sulphate hexahydrate | 0.02 |
| Tween 80 | 0.5 |

Note:
The carbon source would vary according to end product requirement.

EXAMPLE 1

Batch Fermentation of Xylose by *L. buchneri*

The fermentation studies were initially conducted with *L. buchneri* ATCC 4005 in batch serum bottles with a working volume of 0.05 L. The composition used was adopted from previous batch studies on *L. buchneri* reported in the literature (Elferink et al, 2001; Liu et al, 2008). The serum bottles were purged for 1-3 minutes with nitrogen gas of 99.95% purity, and capped using aluminum crimp caps with silicone rubber septa. The bottles were autoclaved for 15 minutes at 120° C., prior to inoculation. The inoculum size used was 3% throughout all the experiments. The serum bottles were incubated at 36° C. in an orbital shaker at 150 rpm for a period of 32-40 h.

A mid log phase culture of L. buchneri from serum bottle was used as a seed inoculum for bioreactor studies. A 1.3-L fermentor with a working volume of 1 L with automated pH and temperature controller (Bioflo 115, New Brunswick Scientific Inc.) was used for free cell fermentation. Batch fermentation was conducted using modified MRS medium consisting of 2.0 g L-1 of Casamino acids, 2.0 g L-1 of Lab-Lemco Powder (oxoid), 3.0 g L-1 of peptone, 5.0 g L-1 of yeast extract, 1.0 g L-1 of sodium acetate, 0.5 g L-1 of K2HPO4, 1.5 g L-1 of $NH_4H_2PO_4$, 0.2 g L-1 of MgSO4.7H2O, 0.1 g L-1 of MnSO4.4H2O, 0.05 g L-1 of CuSO4.6H2O and 0.5 mL of Tween 80. Xylose was used as the carbon source. During fermentations, the temperature was maintained at 36° C., the agitation speed was set at 150 rpm and the pH was maintained at 4.22±0.02 with addition of 10 M NaOH. Filter sterilized industrial grade N2 was sparged at the rate of 0.2 L min-1 for a short duration (<20 min) through the vessel to obtain anoxic conditions. Normal operation was conducted without N2 sparging.

FIG. 5 presents the results from the batch fermentation experiments. The data indicate that L. buchneri, is able to completely convert the xylose substrate within 35 h of fermentation time. The lactic acid and acetic acid concentrations reached up to 52 and 33 g L-1, respectively, while the biomass yield reached up to 0.1 g dry cells g-1 xylose. Under uncontrolled pH conditions, fermentations have been conducted with L. buchneri up to a pH of 3.42, though the conversion rate is somewhat decreased at the lower pH.

EXAMPLE 2

Continuous Fermentation of Xylose by L. buchneri Immobilized on Inorganic Fibers A known weight of sterile alumina fibers (2% w/v) coated with chitosan was introduced in to a batch grown culture fed with 48 g $L^{-1}$ of xylose. Fed batch was accomplished with addition of 25 g $L^{-1}$ of xylose. The reactor was shifted to continuous mode after xylose concertation was reduced to less than 0.5%. The feed medium used for continuous immobilized cell operation consisted of 2.0 g $L^{-1}$ of peptone, 3.0 g $L^{-1}$ of yeast extract, 0.5 g $L^{-1}$ of sodium acetate, 0.2 g $L^{-1}$ of $K_2HPO_4$, 0.2 g $L^{-1}$ of $NH_4H_2PO_4$ and 0.2 g $L^{-1}$ of $MgSO_4.7H_2O$. The feed flow rate was varied according to the run and required dilution rate was obtained using the Masterflex peristaltic pump. A sterile filter membrane cloth tied with cheesecloth was used in the suction line to prevent the loss of alumina fibers. Intermittent purging of nitrogen was done to prevent clogging at membrane. A total reaction volume of 0.9 L and pH of 4.22±0.02 was maintained throughout the fermentation. Minimal stirring (approximately 70-120 RPM) was used to prevent excessive shear disruption of the attached bacterial matrix.

Figure 12:
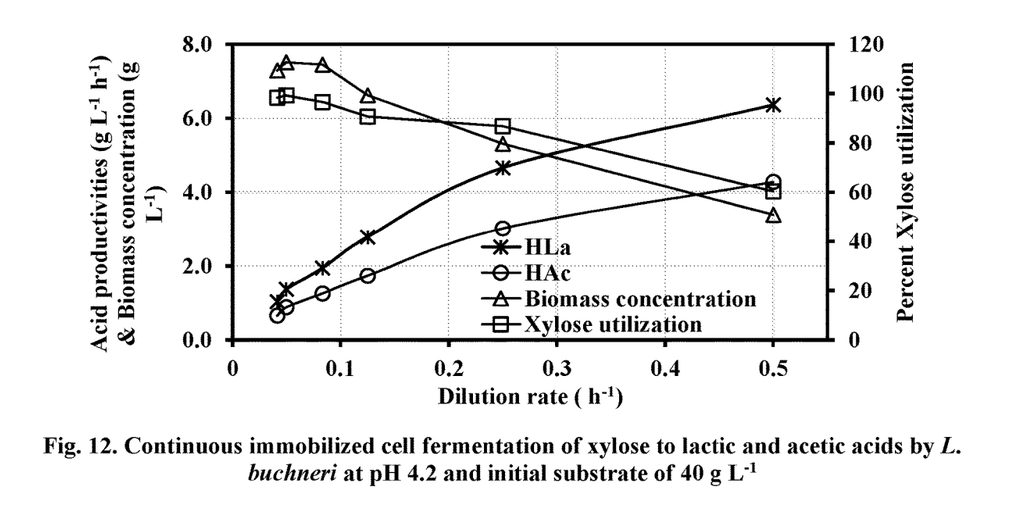
FIG. 12. This graph shows pertains to immobilized cell fermentation using alumina fibers at pH 4.2. The graph shows lactic acid and acetic acid productivities, and xylose conversion rates as a function of the dilution rate.

FIG. 12 displays the results for acid productivities and xylose conversion at various dilution rates. from continuous fermentation with cells immobilized on inorganic fibers. The data indicate that a high lactic acid productivity of 2.8 g $L^{-1}$ $h^{-1}$ for lactic acid and 1.7 g $L^{-1}$ $h^{-1}$ for acetic acid with 96% xylose conversion can be obtained immobilized cell fermentation at a dilution rate of 0.12 $h^{-1}$. High productivities up to 6 g $L^{-1}$ $h^{-1}$ of lactic acid and 4.5 g L-1 h-1 of acetic acid could be achieved using immobilized fermentation at a dilution rate of 0.5 $h^{-1}$. Though the xylose utilization at this dilution rate is less at 60%, the unutilized sugar can be recycled after acid separation as shown in the process flow sheet in FIG. 1.

EXAMPLE 3

Fed-Batch Fermentation of Xylose by L. buchneri Immobilized on Cheese Cloth

Figure 13:
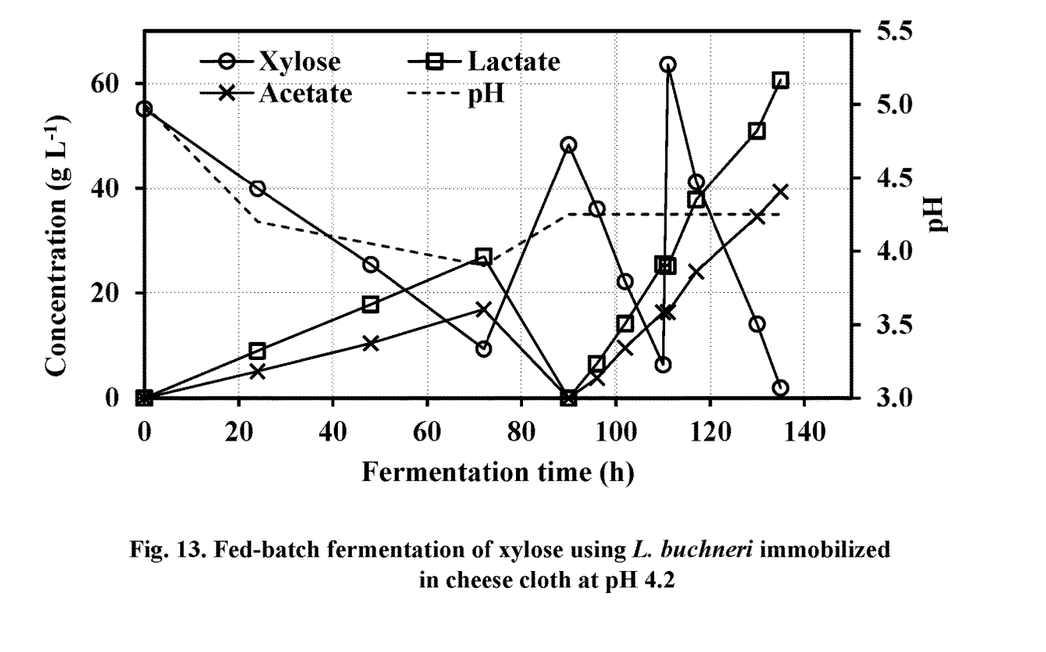
FIG. 13. This figure pertains to immobilized cell fermentation using cheese cloth as the support medium for L. buchneri immobilization. The graph show fed-batch fermentation of xylose at pH ~4.2.

Approximately 1.1 $m^2$ of cheese cloth was wound around the propeller blades, sparging tube, and the sampling tube of the 2 L bioreactor. The reactor was charged with sterile medium, and inoculated with L. buchneri cells. The total working volume was 1.8 L. The fermentation pH was 4.2. The bacteria completely immobilized the cloth matrix resulting in a more clear fermentation broth, and eliminating the need for expensive filtration/clarification steps downstream. The stirring rate was reduced to 70 RPM or less to minimize shear and cell detachment. The results shown in FIG. 13 indicate that L. buchneri cells immobilized on cheese cloth tolerate high lactic and acetic acid concentrations of ~60 g/L and 40 g/L respectively at a pH of 4.2. These high concentrations will reduce downstream processing costs in the separation and concentration of the acids.

EXAMPLE 4

Batch Fermentation of Whey and Lactose by L. buchneri

A concentrated seed culture of L. buchneri grown in 2% glucose, 2% xylose and 0.5% lactose was used as inoculum for batch fermentation of lactose. The lactose fermentation was carried out in a fermenter with a working volume of 1.0 L at an initial pH of 5.0 and the pH was allowed to drop gradually via fermentation to 4.25 and maintained at 4.25 thereafter by the addition of 10 M NaOH. Fermentation temperature was 36° C., and the impeller speed was 150 rpm. The nutrient media composition is similar to that outlined in Table 1, where lactose was used as a major carbon source supplemented with 0.3% of each of glucose and xylose. Filter-sterilized industrial grade $N_2$ was sparged at the rate of 0.2 L $min^{-1}$ for a short duration (≤20 min) through the vessel initially to obtain anoxic conditions. Further operation was conducted without $N_2$ sparging. The fermentation with lactose of initial concentration 60 g $L^-$, resulted in 20 g $L^{-1}$ of propylene glycol, 18 g $L^{-1}$ of acetic acid, 10 g $L^{-1}$ of lactic acid and 2.5 g $L^{-1}$ of ethanol (FIG. 8).

EXAMPLE 5

Batch Fermentation of Whey Permeate and Whey Permeate Powder by L. buchneri

Fermentation of whey was carried out in 0.05 L serum bottles with initial pH at 5.0. The whey permeate obtained from Kansas State University dairy cheese processing operation was heat treated, centrifuged, and filtered prior to use. Whey permeate powder from Foremost Farms, USA was mixed with warm water to obtain lactose concentration equal to 5.3%. The constituents of whey permeate powder can be obtained at www.formostfarms.com. Nutrient media used for the study was as outlined in Table 1. In either case the nutrient constituents were dissolved in clarified whey permeate solution. The bottle headspace were purged with $N_2$ for 1 to 3 minutes, and sealed using aluminum crimp cap and silicone rubber lined septa. The setup was sterilized at 121° C. prior to inoculation. A concentrated seed culture of L. buchneri grown in 2% glucose, 2% xylose and 0.5% lactose was used as the inoculum for batch fermentation of whey permeate. The fermentation was carried out at 36° C. and mixer speed at 150 rpm. The final pH of fermentation was between 3.5 and 4.0. Table 2 lists the product composition for whey permeate and whey permeate powder fermentation at 96 h. The data show that *L. buchneri* can utilize the lactose in whey permeate or whey permeate powder to produce lactate, acetate and propylene glycol.

TABLE 2

Analysis of broth after 96 h fermentation of whey permeate and whey powder from by *L. buchneri*, ATCC 4055

| Whey permeate from cheese production: 5.3% lactose; 0.25% lactate | | Whey permeate powder obtained from Foremost Farms*: 5.3% lactose | |
|---|---|---|---|
| Final media composition | Concentration g/L | Final media composition | Concentration g/L |
| Lactose | 2.4 | Lactose | 5.3 |
| Lactate | 9.5 | Lactate | 9.1 |
| Acetate | 12.5 | Acetate | 12.6 |
| PG | 13.4 | PG | 14.2 |
| EtOH | 3.2 | EtOH | 0 |

*www.foremostfarms.com

Batch fermentation of whey powder was carried out in a fermenter with a working volume of 1.0 L at an initial pH of 5.0. The pH was allowed to drop gradually via fermentation to 4.25 and maintained at 4.25 thereafter with addition of 10 M NaOH. Fermentation temperature was 36° C., and the impeller speed was 150 rpm. The nutrient media composition is similar to that outlined in Table 1, where whey powder containing lactose was used as a major carbon source supplemented with 0.3% of each glucose and xylose. Filter sterilized industrial grade $N_2$ was sparged at the rate of 0.2 L min$^{-1}$ for a short duration (≤20 min) through the vessel initially to obtain anoxic conditions. Further operation was conducted without $N_2$ sparging. FIG. 14 shows that with whey powder, the product concentrations obtained from 50 g/L lactose feed concentration were 15.5 g L$^{-1}$ propylene glycol, 13.5 g L$^{-1}$ of acetate, and 2.7 g L$^{-1}$ of ethanol.

What is claimed is:

1. A process for producing organic deicers comprising:
   (a) incubating an acid-tolerant *Lactobacillus buchneri* in a nutrient medium containing xylose at an incubation pH of 4.3 or less, and at a temperature of at least 30° C. to produce a solution containing at least 30 g/L of acetic acid and 50 g/L of lactic acid,
   (b) incubating, *Propionibacterium acidipropionici*, in sequential fermentation using a spent medium from (a) at an incubation pH of 5.0 to 5.5, and at temperature of at least 35° C. to produce a solution of at least 20 g/L of propionic acid and 10 g/L acetic acid;
   (c) recovering free acetic and propionic acids; and
   (d) reacting the acetic acid or a combination of acetic and propionic acids with, calcium, magnesium, potassium salts or a combination thereof to produce organic deicers.

2. The process of claim 1 wherein the incubation is conducted using free cells suspended in batch, fed-batch, or continuous bioreactors.

3. The process of claim 2 wherein the incubation is conducted using cells immobilized on alumina fibers or fibrous cloth material in the batch, fed-batch or continuous reactors.

4. The process of claim 1 or claim 2 wherein the incubation step (b) is conducted using co-culture of *Lactobacillus dioliovorans* and *Propionibacterium acdipropionici*.

5. The process of claim 1 wherein the xylose fermentation is at least 99% complete, and the volumetric productivity is at least 1.35 g/Lh for lactic acid, and at least 0.85 g/Lh for acetic acid.

6. The process of claim 1 or 2 wherein the nutrient medium contains at least 50 g/L carbohydrate.

7. A process for producing deicers comprising:
   (a) incubating an acid-tolerant *Lactobacillus buchneri* in a nutrient medium containing glucose at an incubation pH of 4.3 or less, and at a temperature of at least 30° C. to produce a solution containing at least 50 g/L of lactic acid, 5 g/L of acetic acid, 5 g/L of propylene glycol and 20 g/L of ethanol;
   (b) incubating, *Propionibacterium acidipropionici*, in sequential fermentation using a spent medium from (a) to utilize the lactate at an incubation pH of 5.0 to 5.5, and at temperature of at least 35° C. to produce a solution of at least 20 g/L of propionic acid and 10 g/L acetic acid;
   (c) incubating *Acetobacter aceti*, in a spent medium from (b) at an incubation pH of 4.5 or less to convert the ethanol to acetic acid;
   (d) recovering the propylene glycol;
   (f) recovering the acetic and propionic acids;
   (h) reacting acetic acid or a combination of acetic and propionic acids with, calcium, magnesium, potassium salts or a combination thereof to produce organic deicers.

8. The process of claim 7 wherein the incubation is conducted using free cells suspended in batch, fed-batch, or continuous bioreactors.

9. The process of claim 8 wherein the incubation is conducted using cells immobilized on alumina fibers or fibrous cloth material in the batch, fed-batch or continuous reactors.

10. The process of claim 7 or claim 8 wherein the incubation step (b) is conducted using co-culture of *Lactobacillus dioliovorans* and *Propionibacterium acdipropionici*.

11. The process of claim 7 or 8 wherein the nutrient medium contains at least 50 g/L carbohydrate.

12. A process for producing organic deicers comprising:
   (a) incubating an acid-tolerant *Lactobacillus buchneri* in a nutrient medium containing lactose at an incubation pH of 4.3 or less, and at a temperature of at least 30° C. to produce a solution containing at least 25 g/L of acetic acid and 30 g/L of propylene;
   (b) incubating an acid tolerant *Lactobacillus dioliovorans*, in sequential fermentation using a spent medium from (a) or as a coculture in the medium of step (a) to produce a solution of at least 10 g/L of each propionic acid and propanol;
   (c) recovering the propionic acids; and
   (d) reacting the propionic acids with, calcium, magnesium, potassium salts or a combination thereof to produce organic deicers.

13. The process of claim 12 wherein the incubation is conducted using free cells suspended in batch, fed-batch, or continuous bioreactors.

14. The process of claim 13 wherein the incubation is conducted using cells immobilized on alumina fibers or fibrous cloth material in the batch, fed-batch or continuous reactors.

15. The process of claim 12 or 13 wherein the nutrient medium contains whey permeate with at least 40 g/L of lactose.

16. The process of claim 12 wherein the nutrient medium of step (a) contains lactate from 1st stage fermentation of sugars by *Lactobacillus plantarum* or other lactate producing bacteria.

17. The process of claim 12 or 13 wherein the nutrient medium contains at least 50 g/L carbohydrate.

\* \* \* \* \*